United States Patent
Kalkote et al.

(10) Patent No.: US 6,818,786 B2
(45) Date of Patent: Nov. 16, 2004

(54) PROCESS FOR THE PREPARATION OF ETHYL 3-ETHOXY-4-ETHOXYCARBONYL-PHENYLACETATE

(75) Inventors: Uttam R. Kalkote, Maharashtra (IN); Mukund K. Gurjar, Maharashtra (IN); Shreerang V. Joshi, Maharashtra (IN); Suresh M. Kadam, Maharashtra (IN); Sanjay J. Naik, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 15 days.

(21) Appl. No.: 10/402,255

(22) Filed: Mar. 31, 2003

(65) Prior Publication Data

US 2004/0192955 A1 Sep. 30, 2004

(51) Int. Cl.[7] ........................ C07C 69/76; C07C 51/10
(52) U.S. Cl. ........................ 560/103; 560/8; 562/405; 562/406
(58) Field of Search ................. 560/8, 55, 76, 560/77, 103

(56) References Cited

U.S. PATENT DOCUMENTS 6,686,497 B1 * 2/2004 Salman et al. ............... 560/64

* cited by examiner

*Primary Examiner*—Shailendra Kumar
*Assistant Examiner*—Karl Puttlitz
(74) *Attorney, Agent, or Firm*—Nixon & Vanderhye P.C.

(57) ABSTRACT

The present invention relates to a process for the preparation of ethyl 3-ethoxy-4-ethoxycarbonyl-phenylacetate having formula 1

Formula 1

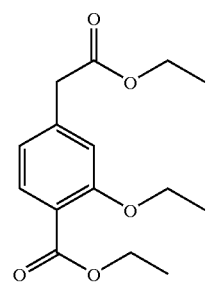

Ethyl 3-ethoxy-4-ethoxycarbonyl-phenylacetate (1) is an important key intermediate for the synthesis of repaglinide (2) an oral hypoglycemic agent Formula 2

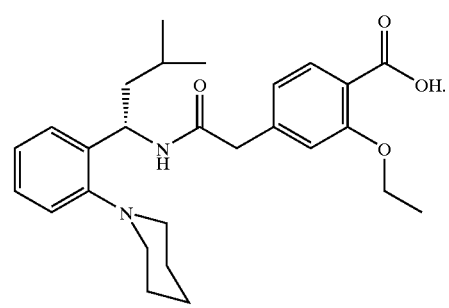

8 Claims, No Drawings

PROCESS FOR THE PREPARATION OF ETHYL 3-ETHOXY-4-ETHOXYCARBONYL-PHENYLACETATE

FIELD OF THE INVENTION

The present invention relates to a process for the preparation of ethyl 3-ethoxy4-ethoxycarbonyl-phenylacetate having formula 1.

Formula 1

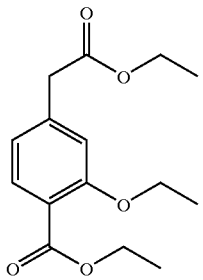

Ethyl 3-ethoxy-4-ethoxycarbonyl-phenylacetate (1) is an important key intermediate for the synthesis of repaglinide (2) an oral hypoglycemic agent.

Formula 2

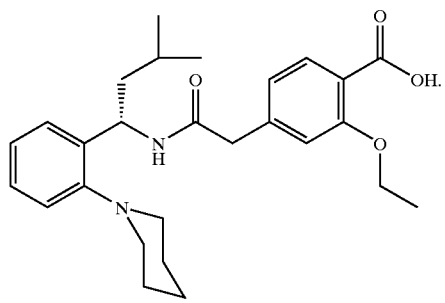

BACKGROUND OF THE INVENTION

Repaglinide (+) 2 ethoxy-4[N-{1-(2-piperidinophenyl)3-methyll-butyl}aminocarbonyl methyl]benzoicacid having formula 2 is from a class of hypoglycemic agents for type II non insulin dependant diabetes mellitus.

Hitherto known process for the preparation of ethyl 3-ethoxy-4-ethoxycarbonyl-phenylacetate having formula 1 involves two methods as shown below Route 1 (J. Med. Chem. 1998, 41, 5219)

1. Alkylation of 4-methylsalicylic acid with ethyl bromide at 150° C. for 30 hrs in autoclave to give ethyl 2-ethoxy-4-methyl benzoate of formula 3.

Formula 3

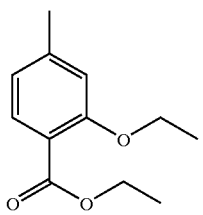

2. Bromination of ethyl 2-ethoxy-4-methyl benzoate of Formula 3 with N-bromo succinamide to give ethyl 4-bromomethyl-2-ethoxybenzoate of formula 4.

Formula 4

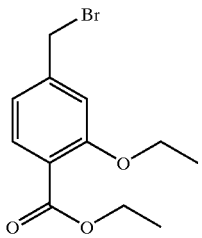

3. Cyanation of compound of formula 4 with sodium cyanide to give ethyl-4-cyanomethyl-2-ethoxybenzoate of formula 5.

Formula 5

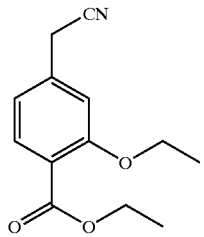

4. Treatment of gaseous HCL with ethyl-4-cyanomethyl-2-ethoxybenzoate in ethyl alcohol to give ethyl 3-ethoxy-4-ethoxycarbonyl-phenylacetate of formula 1.

Formula 1

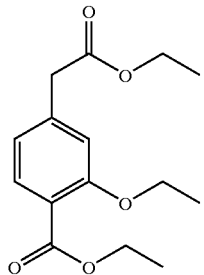

Route 2 (PCT WO 01/3590, 2001)

1. Alkylation of 4-methylsalicylic acid with ethyl bromide in dimethyl sulfoxide to yield ethyl-2-ethoxy-4-methylbenzoate of formula 3.

Formula 3

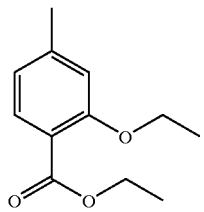

2. Carbonylation of ethyl-2-ethoxy-4-methylbenzoate with lithium diisopropyl amide and carbon dioxide at −80° C. in presence of HMPA gave 3-ethoxy-4-ethoxycarbonyl-phenylacetic acid of formula 6.

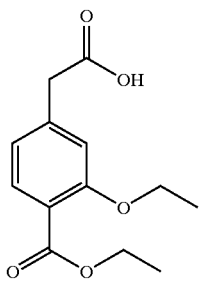

Formula 6

The prior art processes have following drawbacks.

a. The alkylation of 4-methylsalicylic acid involves the use of ethyl bromide which is low boiling reagent, inconvenient for industrial handling.

b. The alkylation of 4-methylsalicylic acid requires dimethylsulfoxide solvent which is not safe for industrial scale.

c. The alkylation reaction requires high pressure and long duration.

d. The use of with lithium diisopropylamide reaction is not easier to handle on industrial scale.

OBJECTS OF THE INVENTION

The main object of the present invention is to provide a new process for the preparation of ethyl 3-ethoxy-4-ethoxycarbonyl-phenylacetate of formula 1 which obviates the drawbacks of the prior art processes and use cheaper and easily available chemicals.

SUMMARY OF INVENTION

Accordingly the present invention provide a new process for the preparation of ethyl 3-ethoxy-4-ethoxycarbonyl-phenylacetate of formula 1 which comprises a. reacting 4-methylsalicylic acid with diethyl sulfate in presence of potassium carbonate in polar organic solvent at a temperature in the range of 50–80° C. for a time period in the range of 6–12 hrs, filtering the product obtained, removing the organic solvent by evaporation and distilling the residue to obtain ethyl-2-ethoxy-4-methylbenzoate of formula 3.

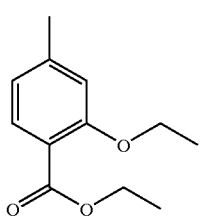

Formula 3 b. brominating ethyl-2-ethoxy-4-methylbenzoate of formula 3 with a brominating agent in organic solvent at temperature in the range of 40–60° C. to obtain ethyl-4-bromomethyl-2-ethoxy benzoate of formula 4.

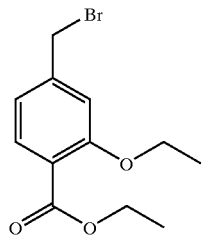

Formula 4 c. Reacting ethyl-4-bromomethyl-2-ethoxy benzoate with CO in ethyl alcohol at a temperature in the range of 30–50° C. for the period in the range of 14–24 hrs, in the presence of a palladium catalyst, removing the solvent by evaporation to obtain ethyl 3-ethoxy-4-ethoxycarbonyl-phenylacetate of formula 1

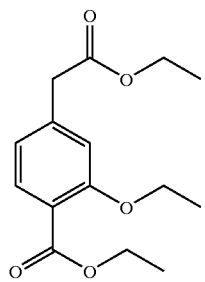

Formula 1

In one embodiment of the invention the organic solvent used in step (a) for the reaction is selected from the group consisting of acetonitrile, acetone and dioxane.

In another embodiment of the invention the brominating agent used in step (b) is selected from 1,3-dibromo-5,4-dimethylhydantoin and N-bromosuccinamide.

In another embodiment of the invention the palladium catalyst used is selected from dichlorobis(1,2,5-triphenylphosphole)palladium and dichlorobis-(tripbenylphosphine)palladium.

DETAILED DESCRIPTION OF THE INVENTION

The present invention provide a new process for the preparation of ethyl 3-ethoxy-4-ethoxycarbonyl-phenylacetate of formula 1 which comprises a. reacting 4-methylsalicylic acid with diethyl sulfate in presence of potassium carbonate in polar organic solvent at a temperature in the range of 50–80° C. for a time period in the range of 6–12 hrs, filtering the product obtained, removing the organic solvent by evaporation and distilling the residue to obtain ethyl-2-ethoxy-4-methylbenzoate of formula 3.

b. brominating ethyl-2-ethoxy-4-methylbenzoate of formula 3 with a brominating agent in organic solvent at temperature in the range of 40–60° C. to obtain ethyl-4-bromomethyl-2-ethoxy benzoate of formula 4.

c. reacting ethyl-4-bromomethyl-2-ethoxy benzoate with CO in ethyl alcohol at a temperature in the range of 30–50° C. for the period in the range of 14–24 hrs, in the presence of a palladium catalyst, removing the solvent by evaporation to obtain ethyl 3-ethoxy-4-ethoxycarbonyl-phenylacetate of formula 1

The organic solvent used in step (a) for the reaction is selected from the group consisting of acetonitrile, acetone and dioxane. The brominating agent used in step (b) is selected from 1,3-dibromo-5,4-dimethylhydantoin and N-bromosuccinamide. The palladium catalyst used is selected from dichlorobis(1,2,5-triphenylphosphole) palladium and dichlorobis-(triphenylphosphine)palladium prepared by procedure reported in literature [B. M. Choudhary & N. Prabhakar Reddy, *Polyhydron*, 5, 911 (1986); T. Okano, I. Uchida, T. Nakagaki, H. Konishi, *J. Molecular catalysts*, 54, 65 (1989)].

The process of the present invention is described herein below with reference to the following examples which are illustrative and should not be construed as limiting the scope of the present invention in any manner.

EXAMPLE 1

4-Methyl salicylic acid (5 g, 32.89 mole), diethyl sulfate (20.26 g, 0.131 mmole) and anhydrous potassium carbonate (18.15 g, 0.132 mole) were mixed thoroughly in dry acetonitrile and mixture was refluxed for 12 hr. Reaction mixture was cooled and filtered through Celite bed. Filtrate was concentrated under vacuum. Residue was purified by fractional distillation at 0.5 mm vacuum. 1st fraction distilled at 48–51° C. (oil bath temperature 80° C.). Product (ethyl-2-ethoxy-4-methylbenzoate) 3 distilled at 90–93° C. (oil bath temperature 120° C.) Yield=6 g (87%).

$^1$HNMR CDCl$_3$ (Spectrum 1) 1.35(t, 3H), 1.45(t, 3H), 2.35(s, 3H), 4.07(q, 2H), 4.34(q, 2H), 6.75(s, 1H), 6.77(d, 1H), 7.70(d, 1H)

GC Conditions

Column: HP1

Temperature: 100–200° C.,

Diethyl sulphate: 0.48 RT

Product 3: 4.09 RT

EXAMPLE 2

4-Methyl salicylic acid (5 g, 32.99 mmol), diethyl sulfate (20.26 g, 0.131 mole) and anhydrous potassium carbonate (18.15 g. 0.132 mole), were mixed thoroughly in dry dioxane and mixture was refluxed for 16 hr. Reaction mixture was cooled and filtered through Celite bed. Filtrate was concentrated under vacuum. Residue was purified by fractional distillation at 0.5 mm vacuum. 1st fraction distilled at 48–51° C. (oil bath temperature 80° C.). Product (ethyl-2-ethoxy4-methylbenzoate) 3 distilled at 90–93° C. (oil bath temperature 120° C.) Yield=5.9 g (84%).

EXAMPLE 3

4-Methyl salicylic acid (5 g, 32.89 mmol), diethyl sulfate (20.26 g, 0.131 mole) and anhydrous potassium carbonate (18.15 g, 0.132 mole) were mixed thoroughly in dry acetone and mixture was refluxed for 16 hr. Reaction mixture was cooled and filtered through Celite bed. Filtrate was concentrated under vacuum. Residue was purified by fractional distillation at 0.5 mm vacuum. 1st fraction distilled at 48–51° C. (oil bath temperature 80° C.). Product (ethyl-2-ethoxy-4-methylbenzoate) 3 distilled at 90–93° C. (oil bath temperature 120° C.) Yield=5.2 g (75%)

EXAMPLE 4

Ethyl-2-ethoxy-4-methylbenzoate (3, 5 g, 24 mmol), freshly recrystallized N-bromosuccinimide (4.7 g, 26.4 mmol), AIBN (30 mg) were mixed in dry carbon tetrachloride (25 ml). Mixture was irradiated with light using 500 W lamp and was refluxed for 12 hr. Reaction mixture was cooled to room temperature and filtered to remove succinimide. Filtrate was washed with water followed by brine wash, dried on anhydrous sodium sulfate and solvent was removed under vacuum. Residue solidifies on keeping. It was dissolved in petroleum.ether (10 ml) by refluxing. Solution was kept at room temperature for 6 hr. Product ethyl 4-bromomethyl-2-ethoxy-benzoate (4) crystallized out as yellow crystals. Cooled in ice bath and filtered. Crystals were washed with ice-cold pet. ether. Dried in air. Yield=3.5 g (50.9%).

$^1$HNMR CDCl$_3$: (Spectrum 2) 1.45(m,6H), 4.12(q, 2H), 4.34(q, 2H), 4.46(s, 2H), 6.97(s, 1H), 6.98(d, 1 H), 7.72(d, 1H)

MS: (Spectrum 3) 287(12%), 286(10%), 208(14%), 161 (47%), 147(24%), 134(100%) 119(16%), 105(28%)

EXAMPLE 5

A mixture ethyl 4-bromomethyl-2-ethoxy-benzoate (4, 1 gm, 3.5 mmol), dichlorobis-(triphenylphosphine)palladium catalyst (0.1 gm), ethyl alcohol (5 ml) was heated to 50° C. with CO for 6–15 hrs. Catalyst was filtered and solvent was removed to yield the product ethyl 3-ethoxy-4-ethoxycarbonyl-phenylacetate (1, 0.75 gm, 2.6 mmol, 76%).

$^1$HNMR CDCl$_3$ 1.26(t, 3H), 1.44(t, 3H), 3.60(s, 2H), 4.18(q, 2H), 4.35(m, 4H), 6.82(d, 1H), 6.90(s, 1H), 7.81(d, 1H).

EXAMPLE 6

A mixture of ethyl 4-bromomethyl-2-ethoxy-benzoate (4, 1 gm, 3.5 mmol), dichlorobis(1,2,5-triphenylphosphole)-palladium catalyst (0.1 gm), ethyl alcohol (5 ml) was heated to 50° C. with CO for 6–15 hrs. Catalyst was filtered and solvent was removed to yield the product ethyl 3-ethoxy-4-ethoxycarbonyl-phenylacetate (1, 0.87 gm, 3.1 mmol, 88%).

We claim:

1. A new process for the preparation of ethyl 3-ethoxy-4-ethoxycarbonyl-phenylacetate of formula 1 which comprises

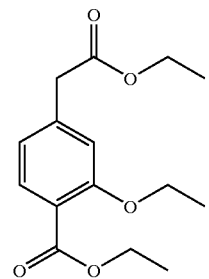

Formula 1 a. reacting 4-methylsalicylic acid with diethyl sulfate in presence of potassium carbonate in a polar organic solvent, filtering a resultant reaction mixture, removing the organic solvent by evaporation and distilling a residue to obtain ethyl-2-ethoxy-4-methylbenzoate of formula 3

Formula 3

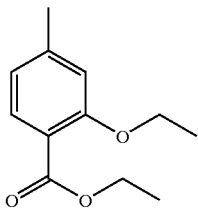

b. a brominating ethyl-2-ethoxy-4-methylbenzoate of formula 3 with brominating agent in an organic solvent to yield ethyl-4-bromomethyl-2-ethoxy benzoate of formula 4

Formula 4

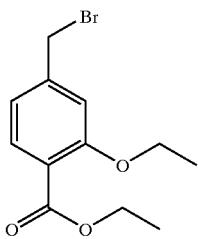

c. reacting ethyl-4-bromomethyl-2-ethoxy benzoate with CO in ethyl alcohol, removing the solvent by evaporation to obtain ethyl 3-ethoxy-4-ethoxycarbonyl-phenylacetate of formula 1.

2. A process claimed in claim 1 wherein the organic solvent used in step (a) is selected from the group consisting of acetonitrile, acetone and dioxane.

3. A process claimed in claim 1 wherein the brominating agent used in step (b) is selected from dibromo dimethyl-hydantoin and N-bromosuccinimide.

4. A process claimed in claim 1 wherein a palladium catalyst is used in step c and is selected from dichlorobis (1,2,5-triphenylphosphole)-palladium or dichlorobis-(triphenylphosphine)palladium.

5. A process as claimed in claim 1 wherein step (a) is carried out at a temperature in the range of 50 to 80° C. and for a time period in the range of 6 to 12 hours.

6. A process as claimed in claim 1 wherein step (b) is carried out at a temperature in the range of 40 to 60° C.

7. A process as claimed in claim 1 wherein step (c) is carried out at a temperature in the range of 30 to 50° C. and for a time period in the range of 14 to 24 hours.

8. A process as claimed in claim 1 wherein the solvent used in step (b) comprises carbon tetrachloride.

* * * * *